United States Patent [19]

Schreiber

[11] Patent Number: 5,246,444

[45] Date of Patent: *Sep. 21, 1993

[54] OSTEOTOMY DEVICE AND METHOD

[76] Inventor: Saul N. Schreiber, 6525 N. Central Ave., Phoenix, Ariz. 85012

[ * ] Notice: The portion of the term of this patent subsequent to Jan. 7, 2009 has been disclaimed.

[21] Appl. No.: 749,278

[22] Filed: Aug. 23, 1991

Related U.S. Application Data

[63] Continuation-in-part of Ser. No. 461,830, Jan. 8, 1990.

[51] Int. Cl.$^5$ ............................................. A61F 5/00
[52] U.S. Cl. ....................................... 606/87; 606/96
[58] Field of Search .................................. 606/86–90, 606/96, 97, 98, 104, 105, 79

[56] References Cited

U.S. PATENT DOCUMENTS

| | | | |
|---|---|---|---|
| 4,335,715 | 6/1982 | Kirkley | 606/87 |
| 4,349,018 | 9/1982 | Chambers | 606/88 |
| 4,421,112 | 12/1983 | Mains et al. | 606/88 |
| 4,750,481 | 6/1988 | Reese | 606/87 |
| 4,952,213 | 8/1990 | Bowman et al. | 606/79 |
| 5,078,719 | 1/1992 | Schreiber | 606/87 |

Primary Examiner—Peter A. Aschenbrenner
Attorney, Agent, or Firm—Harry M. Weiss

[57] ABSTRACT

An osteotomy device and method therefor, is provided that allows the surgeon to establish a reference external to the bone as to the position of the apex and angle of the wedge to be cut and then to make use of an integral saw guide to translate those references into the bone as saw cuts which precisely remove the required wedge of bone. Thus this device and method therefor would enable the surgeon to leave a sufficient amount of residual bone after making the cuts into the bone (for example of a wedge of bone) so as to inhibit the fracturing of the bone.

12 Claims, 5 Drawing Sheets

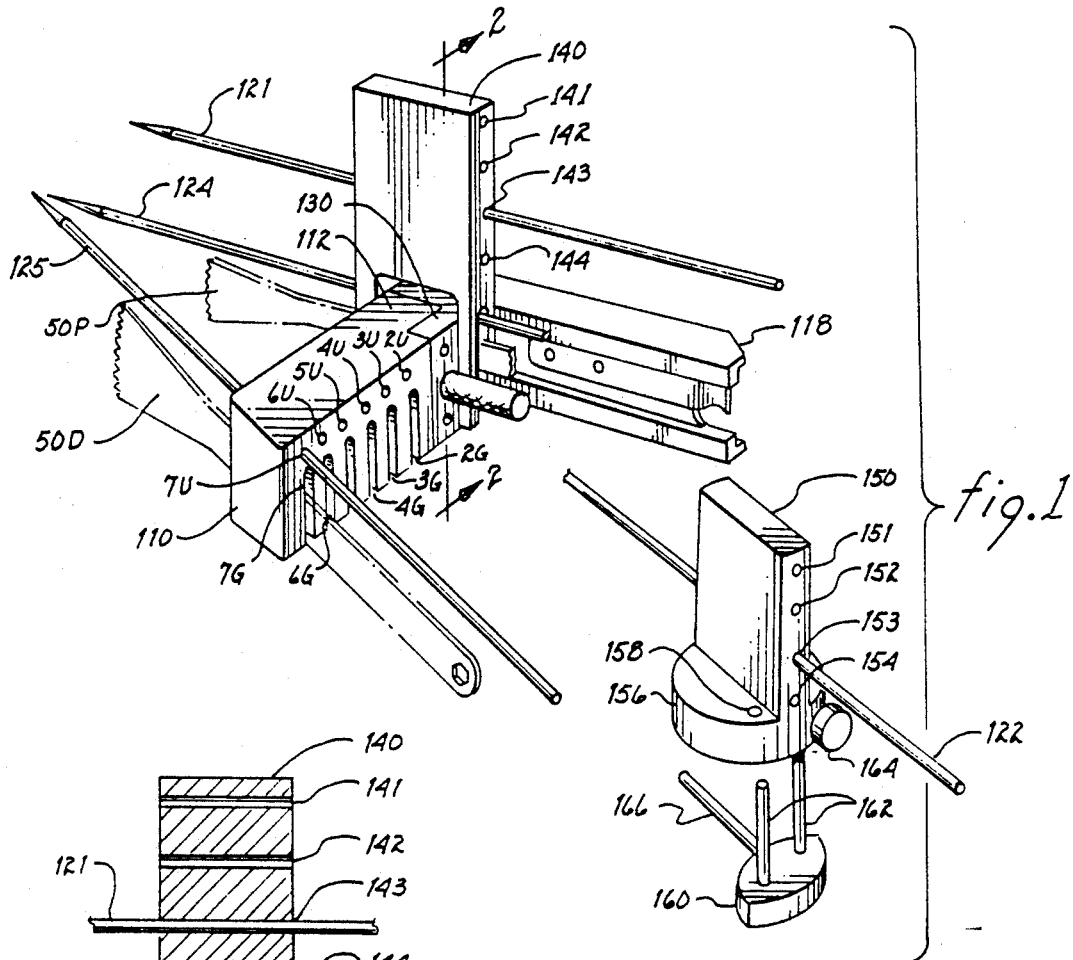
fig. 1
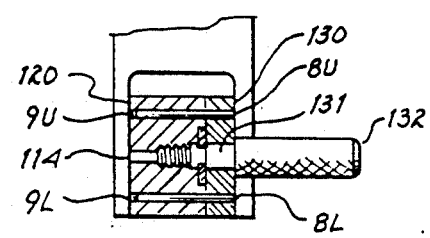
fig. 2
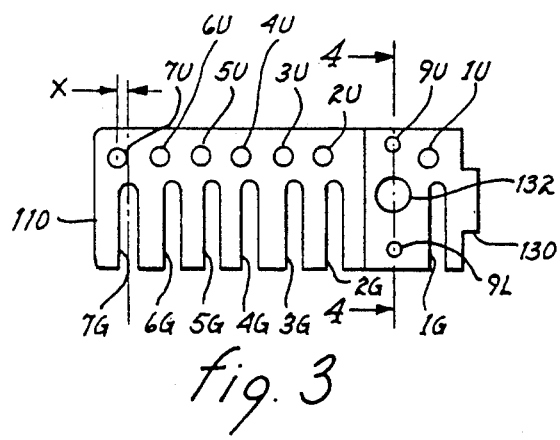
fig. 4
fig. 3

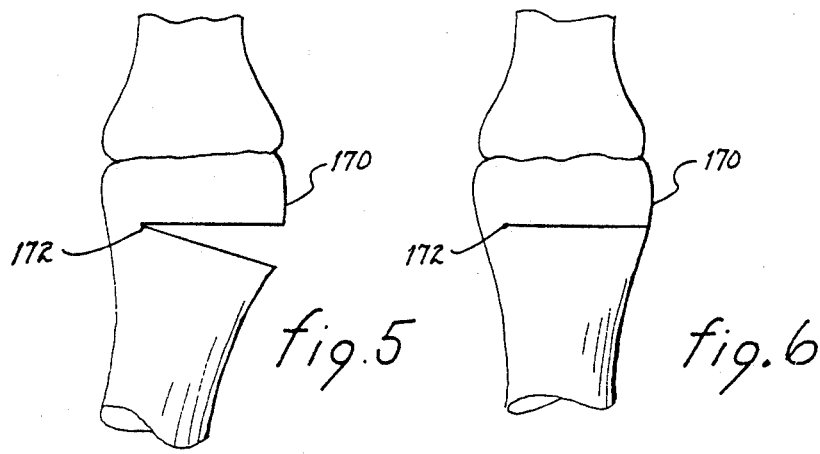
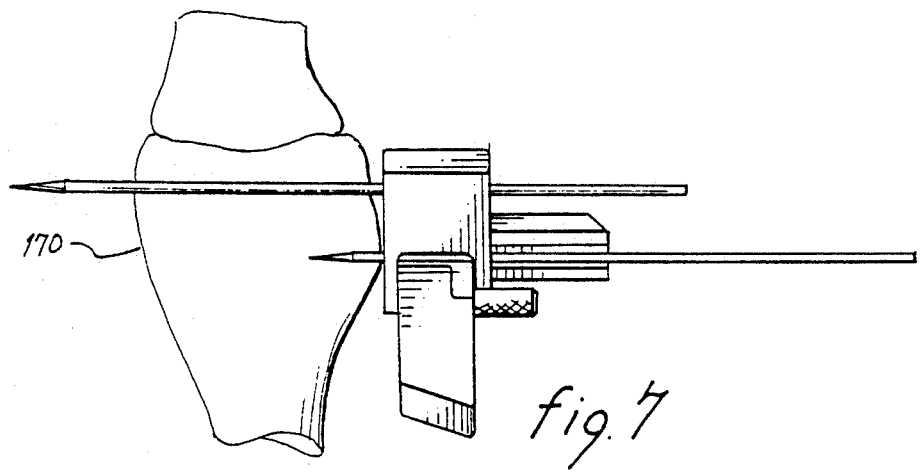
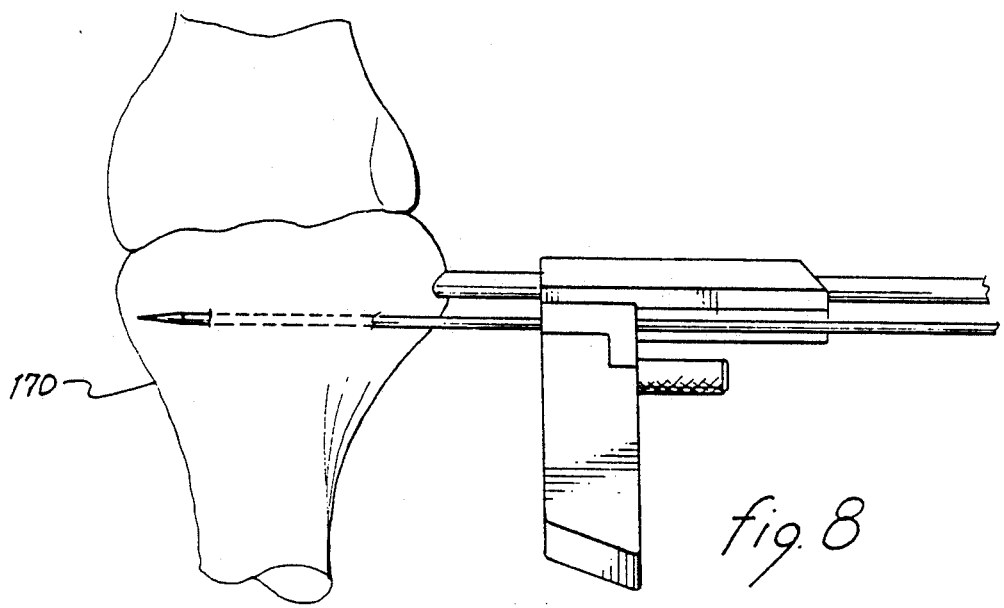

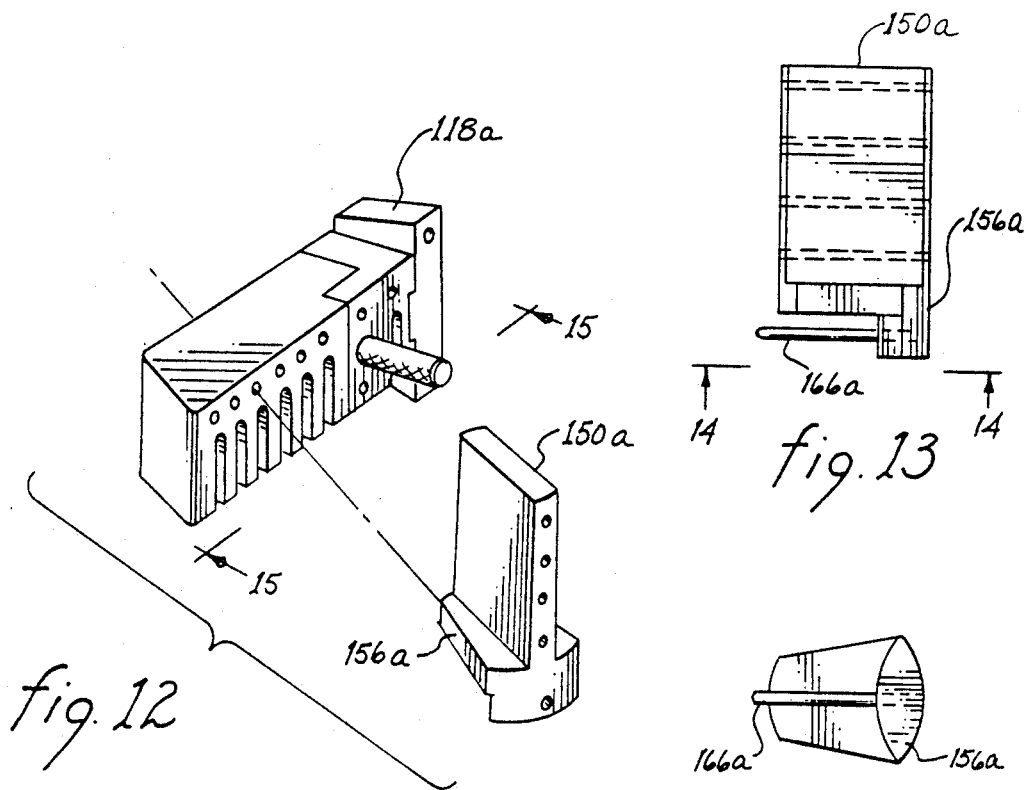
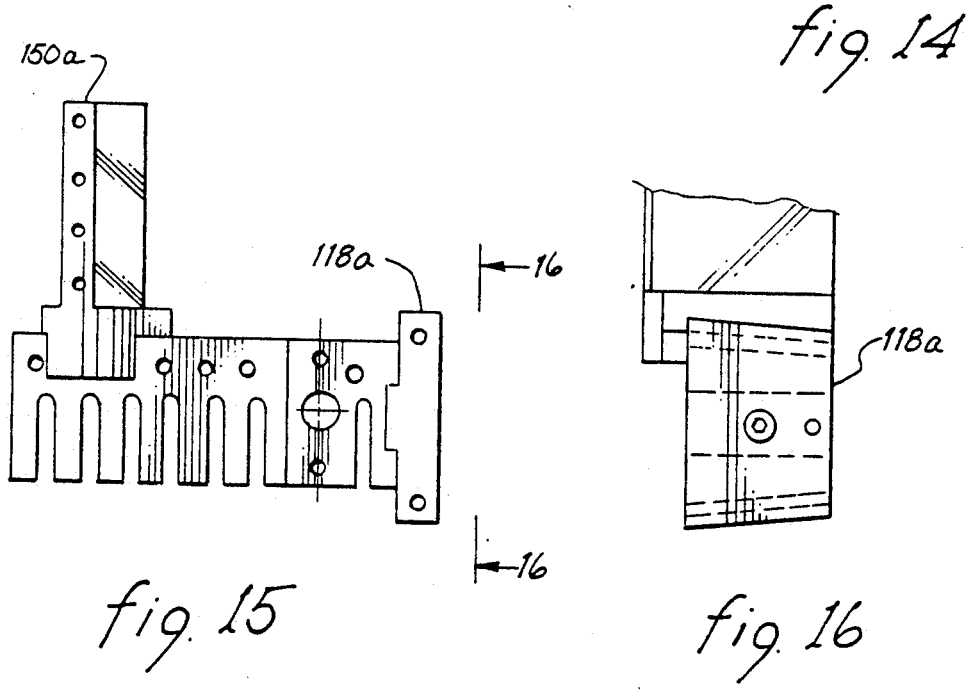

OSTEOTOMY DEVICE AND METHOD

This patent application is a continuation-in-part of Ser. No. 07/461,830 filed Jan. 8, 1990, entitled Osteotomy Device and Method Therefor.

BACKGROUND OF THE INVENTION

This invention relates generally to an osteotomy device and methods for its use. More particularly, this invention relates to an osteotomy device and method in which a rigid block is positioned in alignment with a patient's bone such as a leg bone and saw guides incorporated in this block are used for precisely locating two intersecting bone cuts such as below a person's knee portion so that a bone wedge can be removed so as, for example, to correct for leg deformities such as for bowleggedness.

BACKGROUND OF THE INVENTION

Osteotomy is a surgical procedure which involves cutting and removing a section of bone. The procedure is used to correct many types of bone deformities found in the human leg. For example, in the instance of improper leg formation during growth, undesired angulation or orientation of a particular bone with respect to other bones of the leg often occurs such as the condition referred to as bowleggedness. The surgical procedure for overcoming this type of medical problem normally involves the removal of a wedge-shaped section of the knee portion of the malformed or misaligned leg at a predetermined location which causes the relative repositioning of the remaining bone sections of the leg so as to impart to the surgically corrected leg the proper relative configuration or orientation. The wedge-shaped section removed from the original knee bone is, of course, of a predetermined size which naturally depends upon extent of the correction required. For example, by known techniques, an orthopedic surgeon can determine the extent of leg deformity and the required amount of a wedge that is needed to correct the leg deformity.

To make the correct adjustment to the lege requires not only cutting out the correctly sized bone wedge portion at a proper angle, but also assuring that there remains, at the apex of the wedge, residual bone of sufficient thickness to prevent a complete severance or fracture of the bone and to promote mending together of the cut or bone portions. Also, to ensure correct realignment of the bone, it is essential that the cuts into the bone, performed to remove the wedge-shaped segment, be substantially smooth and planar so that, when the severed end regions of portions of the remaining bone segments are brought into contact their surfaces mate uniformly across the entire severed surfaces to promote rapid and structurally effective mending of the cut bone portion. Furthermore, to assure this rapid mending, often times a suitably shaped blade plate or side plate is coupled, by screws, to the remaining bone segments, after removal of the wedge portion, and is used to hold the segments together. To properly use such a blade plate this requires that the removed wedge portion have a proper angle configuration.

U.S. Pat. No. 4,335,715 issued Jun. 22, 1982 to W. H. Kirkley or "Osteotomy Guide" discloses an apparatus in which a pair of pins positioned on an arcuate track are inserted into the bone to serve as a guide for the surgeon in making cuts into the bone. The device has no means for determining the apex of the wedge. Therefore, the surgeon must reply on his judgment to determine the apex or remove an entire wedge without leaving any residual bone. Obviously, such a procedure complicates the healing process.

U.S. Pat. No. 4,349,018, issued Sep. 14, 1982 to G. R. Chambers for "Osteotomy Apparatus" discloses a fairly complex and cumbersome device for guiding saw cuts in a operation for the total removal of the Knee. Because of the device's complexity it is ill suited to simpler osteotomy procedures.

U.S. Pat. No. 4,627,425, issued Dec. 9, 1986 to H. W. Reese for "Osteotomy Appliances and Method" discloses a guide to be used by the surgeon to make a second cut in a bone at a predetermined angle from a first cut. To locate the apex of the wedge, a pin has to be inserted vertically into the bone. Also, the device produces a wedge without a right angle and therefore cannot be used with the blade plate or side plate described above.

U.S. Pat. No. 4,757,810, issued Jul. 19, 1988 to H. W. Reese for "Osteotomy Apparatus and Method" discloses a guide for precisely locating two parallel, spaced apart bone cuts. This guide however cannot be used to cut a wedge from the bone.

U.S. Pat. No. 4,421,112 issued Dec. 20, 1983 to D. B. Mains et al for "Tibial Osteotomy Guide Assembly and Method" discloses a guide assembly which uses a relatively complex two pairs of parallel guide pins to guide a saw to remove a bone wedge.

Still there is a need for a osteotomy device that would allow a surgeon to remove a pre-calculated sized bone wedge having a proper angle, that would leave a sufficient of residual bone, that does not require drilling a vertical pin into the bone to locate the apex of the wedge and that provides a integral saw guide that would simplify the sawing of the bone wedge.

SUMMARY OF THE INVENTION

An object of the present invention is to provide an osteotomy device with integral saw guide and method therefor for removing a bone wedge having a proper angle.

Another object of the present invention is to provide an osteotomy device with integral saw guide and method thereof that can locate the apex of a bone wedge to be removed without drilling a pin vertically into the bone.

Yet another object of the present invention is to provide an osteotomy device with integral saw guide and method therefor that would enable the surgeon to leave a sufficient amount of residual bone after making the cuts into the bone (for example of a wedge of bone) so as to inhibit the fracturing of the bone.

The subject invention accomplishes these objects by providing a device and method therefor that allows the surgeon to establish a reference external to the bone as to the position of the apex and angle of the wedge to be cut and then to make use of an integral saw guide to translate those references into the bone as saw cut which precisely remove the required wedge of bone.

These and other objects, features and advantages of the present invention, as well as details of the preferred embodiment thereof, will be more fully understood from the following description and drawing.

BRIEF DESCRIPTION OF THE DRAWINGS

FIG. 1 is a perspective view of the osteotomy device of this invention.

FIG. 2 is a cross-sectional view taken along line 2—2 of FIG. 1.

FIG. 3 is front view of block 110 and connecting member 130 of FIG. 1 shown with tower 140 removed.

FIG. 4 is a cross-sectional view taken along line 4—4 of FIG. 3.

FIG. 5 is a vertical side view of a model of a leg bone with a bone wedge removed before straightening out the bottom leg portion.

FIG. 6 is a vertical side view of the same leg model reoriented after the bone wedge has been removed showing the bottom leg portion straightened out with respect to the knee portion.

FIG. 7 is a perspective new of the osteotomy device positioned next to the model of the leg bone after insertion of a first (top pin) therein.

FIG. 8 is a perspective view with the top tower of the osteotomy device of FIG. 7 removed and the lower transverse pins drilled into the bone model.

FIG. 12 is an exploded, perspective view of an alternative embodiment of the osteotomy device in accordance with this invention.

FIG. 13 is a cross-sectional view of tower 150a of the alternative embodiment of FIG. 12.

FIG. 14 is a bottom view taken along line 14—14 of FIG. 13.

FIG. 15 is a cross-sectional view taken along line 15—15 of FIG. 12 showing tower 150a in place and positioning pin 166a engaged.

FIG. 16 is a side view taken along line 16—16 of FIG. 15.

DESCRIPTION OF THE PREFERRED EMBODIMENT

Figure 9:
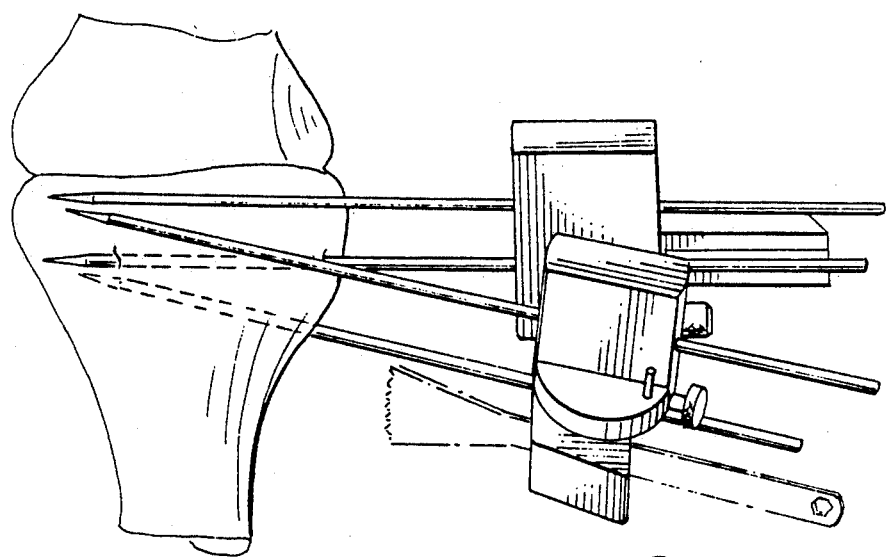
FIG. 9 is a perspective view of the osteotomy device of FIGS. 7 and 8 with an external oblique pin aligned at a predefined angle with the transverse pin.
Figure 10:
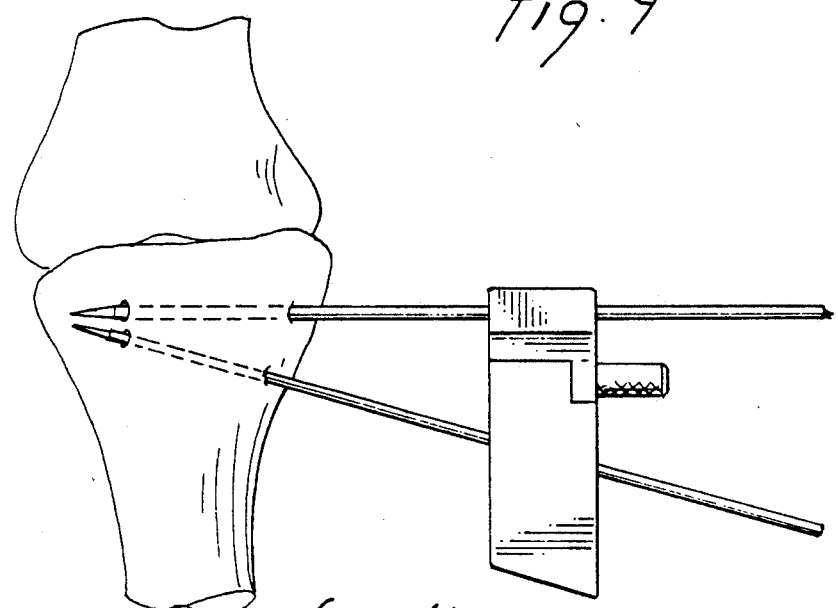
FIG. 10 shows the lower oblique and transverse pins guided by the osteotomy device and drilled in place in the leg bone after the procedure of FIG. 9.

In the preferred embodiment (see FIG. 1) the subject invention comprises a substantially trapezoidal shaped block 110. The distal end 112 of the block 110 is recessed to receive a L-shaped connecting member 130. The distal end 112 has two transverse bores 9U and 9L extending therethrough (see FIG. 4). The two bores 9U and 9L lie in the same vertical plane, which is perpendicular to the length of the block 110. The subscript U indicates the upper bore and the subscript L indicates the lower bore. The distal end 112 also has a threaded hole 114 for receiving a connecting pin 132. Disposed in a horizontal plane are a plurality of oblique bores, 2U, 3U, 4U, 5U, 6U and 7U. The L-shaped connecting member 130 (see FIG. 3) has a transverse bore 1U and a corresponding guide slot 1G. When connecting member 130 is attached to block 110, bore 1U is in the same horizontal plane as bores 2U, 3U, 4U, 5U, 6U and 7U in block 110. The plurality of guide slots 1G–7G are disposed in a plurality of vertical planes each parallel to vertical planes through each of the center axes of the transverse bore 1U and the oblique bores 2U–7U. The plurality of guide slots are positioned so that the proximal interior face of each guide slot is displaced a horizontal distance X from the vertical plane through the center axis of its corresponding bore. The bore-guide slot pair 2U–2G is angled 7½ degrees from the vertical planes passed through bore-guide slot pair 1U–1G. Each succeeding bore-guide slot pair 3U–3G, 4U–4G, etc. is displaced an additional 2½ degrees from the preceding bore-guide slot pair. For example, the pair 3U–3G are angled 2½ degrees from the bores has the same diameter which is selected to tightly receive one of the surgical pins 120. Guide slots 1G–7G are adapted so that any one can hold and guide an osteotomy saw. For example, FIG. 1 shows guide slot 76 holding and guiding an osteotomy saw 50P. The size of each guide slot 1G–7G and the horizontal displacement distance X are chosen to suit the particular requirements of the osteotomy saw 50 appropriate for the surgical procedure.

The L-shaped connecting member 130, (see FIG. 4), also has a threaded hole 131 for receiving the connecting pin 32 and two transverse bores 8U, 8L. The connecting member 130 is sized and shaped so that when it is attached to the distal end 112 of the block 110 by inserting the connecting pin 132 through hole 131 and hole 114, the bores 8U, 8L align with the bores 9U, 9L respectively. A guide 118, for a bone chisel or drill, is attached to the connecting member 130 so that the guide 118 is perpendicular to the block 110. This two part design combining the connecting member 130 to the distal end 112 by the connecting pin 132 allows for fast and easy removal of the guide 118 from the block 110 after the surgical pins 120 have been inserted into the bone without disturbing the position of the inserted surgical pins 120.

A first rectangular tower 140, (see FIG. 2), has four transverse bores 141, 142, 143 and 144 extending therethrough. Each of the bores 141, 142, 143 and 144 are sized to receive one of the surgical pins 120 and lie in the same vertical plane but at different heights. Extending downward from the bottom of the tower 140 are two legs 145. The distance between the two legs 145 is selected to allow the two legs 145 to slip fit over the distal end 112 and connecting member 130 after the connecting member 130 has been attached to the block 110. Each of the 145 has a slit 146 to assure that the legs 145 do not block the traverse bore-guide pair 1U–1G.

A second rectangular tower 150, (see FIG. 1), has four transverse bores 151, 152, 153 and 154 extending therethrough. Each of the bores 151, 152, 153 and 154 are sized to receive one of the surgical pins 120 and lie in the same vertical plane but at different heights. The tower 150 has an ovate base 156 with two vertical holes 158. The two holes 158 are sized to receive two prongs 162 extending upward from an ovate member 160 positioned below the base 156. In the embodiment shown in FIG. 1, the ovate member 160 is shown as a separate piece that is separated from the base 156, however, if desired, the ovate member 160 can be attached, such as by welding, to the base 156. The height of the tower 150 can be adjusted by sliding the base 156 up and down the two prongs 162. The two prongs 162 can be locked into the base 156 by tightening a locking pin 164. Extending horizontally from the ovate member 160 is a prong 166 which is sized to be inserted into any of the guide slots 2G-7G. Prong 166 is coupled to ovate member 160 with a horizontal offset X so that the vertical plane through transverse bores 151-154 coincides with the longitudinal axis of the particular bore 2U-7U corresponding to the particular guide slot into which prong 166 is inserted.

The surgical pins 120 are all of identical length. Each of the pins 120 has a pointed end and is strong enough to be drilled into bone without bending. Four surgical pins 120 are required when using the subject invention. For illustrative purposes only the surgical pins 120 are identified in the drawings and in the following description as follows. Surgical pin 121 is inserted through the bore 143 in the tower 140. Surgical pin 122 is inserted through the bore 153 in the tower 150. Surgical pin 123 is inserted through the bore 1U. Surgical pin 125 is inserted through the bore 7U.

Each of the components of the subject invention is preferably made of metal and can be sterilized.

In the preferred embodiment, (see FIG. 4-10), the subject invention would operate as follows. Starting from the point where all of the components are disassembled, first, the distal end 112 of the block 110 is coupled to the connecting member 130 by inserting the connecting pin 132 through the holes 114 and 131. The guide 118 is then attached to the connecting member 130. This combination of components is positioned adjacent to the subject bone 170 which is illustrated in skeletal form in the drawings. The combination is adjusted until the block 110 is parallel to the bone 170. The tower 140 is then slip fit over the distal end 112 and connecting member 130 so that the bores 141-144 lie in a vertical plane parallel to vertical planes through the longitudinal axes of bore 1U and guide slot 1G. The surgical pin 121 is inserted through the bore 143. The selection of the bore 143 is for illustrative purposes only. In actual operation the choice of which bore to use is determined by the thickness of the soft tissue of the leg. The bore that allows the surgical pin 121 to pass closest to the leg without touching the leg is preferably selected. The surgical pin 121 is inserted through the bore 143 until the surgeon estimates that the tip of the pin 121 is directly above the apex 172 of the bone wedge 174. The position of the pin 121 relative to the apex 172 is then checked by X-rays and any adjustments are made as needed to the position of the pin 121. The surgeon then slides the surgical pin 124 through the bores 1U and drills surgical pin 124 into the leg until the end of pins 124 aligns with the end of the pin 121. Once this procedure is completed the position of the apex 172 of the bone wedge 174 is established. Also, should the device be accidently moved it can always be accurately realigned and sliding the device along pin 124 until the ends of the pins 124 and 121 are once again aligned.

As one skilled in the art would know, the angle of the bone wedge is substantially equal to the angle through which the leg must be rotated to realign the lower leg. Assuming this angle is twenty degrees, the surgeon then inserts the prong 166 through the guide slot 7G. The height of the tower 150 is adjusted until the bore 153 lies at the same height as the bore 143. The locking pin 164 is tightened securing the position of the tower 150. The surgical pin 122 is inserted through the bore 153 until the tip of the pin 122 meets the tip of the pin 121. If these two tips do not meet, the position of pin 121 is adjusted as described above which will result in the two tips meeting. The surgical pin 125 is inserted through the bore 7U and drilled into the bone 170 until the end of the pin 125 aligns with the end of the pin 124. The tower 150 along with the pin 122 is then removed. The tower 140 along with the pin 121 is also removed. Block 110 and connecting member 130 are now securely positioned with respect to bone 170 by surgical pin 124 which has been drilled into bone 170 through transverse bore 1U and by surgical pin 125 which has been drilled into bone 170 through oblique bore 7U. The surgeon now inserts a suitable osteotomy saw 50D into guide slot 1G and makes a first transverse cut into bone 170 thereby forming one face of the bone wedge 174 which is to be removed. The surgeon next inserts a suitable osteotomy saw 50P into guide slot 7G and makes a second oblique cut into bone 170 thereby forming the second face of bone wedge 174. Because of the particular arrangement of the bores, pins and guide slots of the subject invention, the saw cuts which form bone wedge 174 will intersect at precisely the required apex position 172 which will provide the optimum surgical result. After bone wedge 174 has been removed, the connecting pin 132 is unscrewed and the connecting member 130 along with the guide 118 is removed by sliding the connecting backward over the pin 124. The block 110 is then removed by sliding it backwards over the pin 125. Pins 124 and 125 are then removed and the remainder of the surgical procedure is completed.

FIGS. 12-16 shown an alternative embodiment of the subject osteotomy device. The differences between the this alternative embodiment and the preceding embodiment are as follows:

The guide 118 is replaced by the side plate 118a for inserting screws (now shown) into the leg. Both the guide 118 and the side plate 118a are standard equipment used in osteotomy procedures. The base 156a of the second rectangular tower 150a is now integral with the tower 150a. The holes 158, the prongs 162 and the locking pin 164 of the original embodiment have been removed. Prong 166a is now integral with base 156a and is arranged to engage the appropriate one of the oblique bores 2U-7U.

Figure 11:
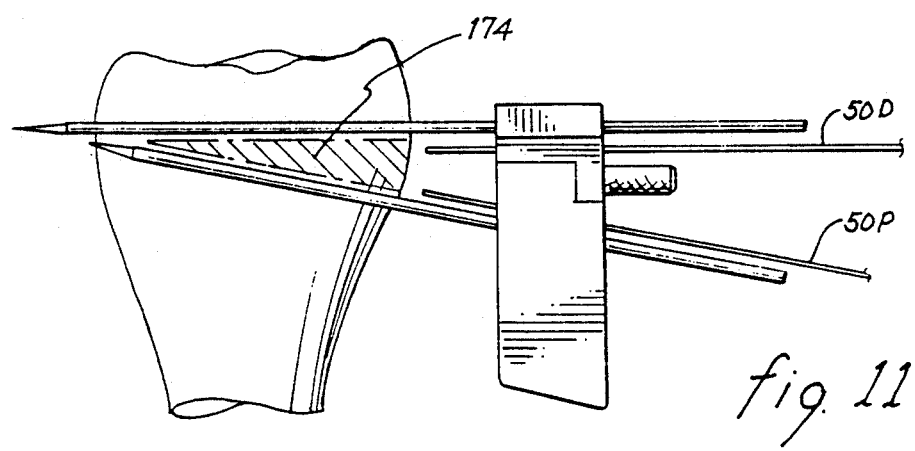
FIG. 11 is a view similar to FIG. 10 with a portion representing the bone wedge to be removed shown in the cross-section.
Figure 17:
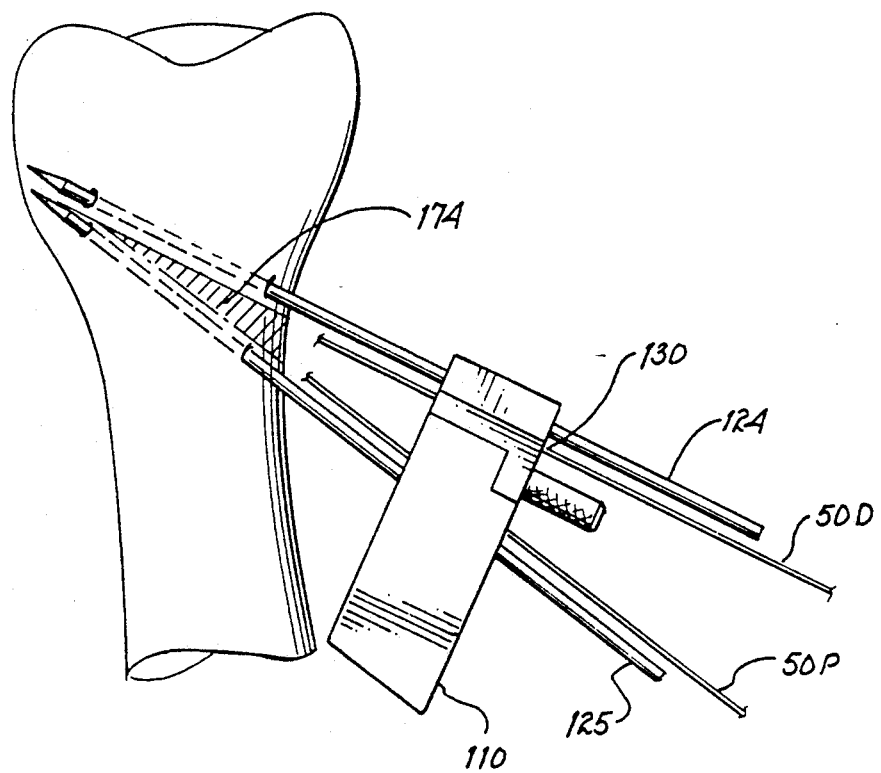
FIG. 17 is a view similar to FIG. 11 showing how the osteotomy device of this invention can be used to remove a bone wedge at an angle and starting from below the tibial tubercle that is located in the knee area below the joint.

FIG. 17 shows another way the osteotomy device of this invention can be used to remove a bone wedge starting from below the tibial tubercle (the technical term to describe the bump below a person's knee) and extending upwardly to an angle a point past the tibial tubercle. Thus, this other application or technique for removing a bone wedge has the following advantages: (1) the area between the tibial tubercle and the knee joint is not substantial impacted or disturbed which permits this critical portion to be better prepared for possible future knee surgery where knee replacement is needed; (2) longer bone wedge surfaces (top and bottom) are provided by this alternative technique thereby permitting better healing and joining together between the newly cut bone surfaces that are joined together after removal of the bone wedge; (3) a greater amount of a bone wedge can be removed using this alternative technique over the technique of removing a bone wedge (see FIG. 11) in the fairly narrow and size limited region between the tibial tubercle and the joint; and (4) a much larger and longer surface area is provided by this alternate technique for better healing.

The osteotomy devices described in the preferred and alternate embodiments can be rotated so that they can be used on both left and right legs.

While the invention has been particularly shown and described with reference to a preferred embodiment thereof, it will be understood by those skilled in the art that changes in form and detail may be made therein without departing from the spirit and the scope of the invention.

I claim:

1. An osteotomy guide used in the removal of a wedge shaped piece of bone from patient's leg, which comprises:

a plurality of surgical pins;

a block having a first transverse bore extending therethrough, a transverse guide slot extending therethrough, a plurality of oblique bores extending therethrough, and a plurality of oblique guide slots extending therethrough, said oblique bores being aligned with said transverse bore in a horizontal plane and said oblique bores and oblique guide slots being positioned at predetermined angles from said transverse bore and transverse guide slot, said transverse and oblique bores being sized to receive said surgical pins and said transverse and oblique slots being sized to receive an osteotomy saw, a first tower member, disposed atop said block and in line with said first transverse bore, and having a plurality of transverse bores sized to receive a number of said surgical pins for extending therethrough; and a second tower member, having a plurality of transverse bores sized to receive a number of said surgical pins for extending therethrough disposed atop said block and coupled to one of said oblique bores so that said transverse bores so that said transverse bores of said second tower are aligned at the same predetermined angle as said oblique bore coupled thereto.

2. The device recited in claim 1 wherein said second tower member has an ovate base, said base having a prong extending therefrom for insertion into any of said oblique bores.

3. The device recited in claim 2 wherein said ovate base is integral with said second tower.

4. The device recited in claim 2 wherein said ovate base is slideably coupled to said second tower.

5. The device recited in claim 4 wherein said second tower has a locking pin means for securing said slidably coupled, ovate base.

6. The device recited in claim 1 further comprising:
   bone cutting means for cutting a channel in said bone of a patient's leg; and
   means for coupling said bone cutting means to said block so that said bone cutting means is positioned perpendicular to said block.

7. The device recited in claim 6 wherein said means for coupling further comprises
   an L-shaped member and
   screw means for screwably coupling said L-shaped member to said bone cutting means and to said block.

8. The device recited in claim 6 wherein said bone cutting means is a bone chisel.

9. The device recited in claim 6 wherein said means for coupling further comprises
   side plate means for placing screws in said bone of a patient's leg and
   screw means for screwably coupling said L-shaped member to said bone cutting means and to said block.

10. The device recited in claim 1 wherein said first tower member has a pair of legs extending downwardly over said block.

11. The device recited in claim 10 wherein each of said legs has a slit extending lengthwise from the bottom of each of said legs to a level which allows access to said transverse guide slot and said first transverse bore.

12. An osteotomy device used in the removal of a wedge shaped piece of bone from a patient's leg bone, comprising:
    block means for establishing a device structure parallel to said patient's leg bone;
    connecting means detachably coupled to said block means for extending the distal end of said device structure;
    first tower means detachably coupled to said connecting means for temporarily extending said device structure;
    first locating pin means coupled to said first tower means for locating external to the leg of said patient the position of a first face of said wedge shaped piece of bone;
    first pin means coupled to said connecting means for drilling into said patient's leg bone along an axis parallel to the longitudinal axis of said first locating pin means
    first guide slot means coupled to said connecting means for guiding an osteotomy saw in cutting said first face of said wedge shaped piece of bone;
    second tower means detachably coupled to said block means for temporarily extending said device structure;
    second locating pin means coupled to said second tower means for locating external to the leg of said patient the position of a second face of said wedge shaped piece of bone;
    second pin means coupled to said connecting means for drilling into said patient's leg bone along an axis parallel to the longitudinal axis of said second locating pin means
    second guide slot means coupled to said connecting means for guiding an osteotomy saw in cutting said second face of said wedge shaped piece of bone.

* * * * *